United States Patent [19]

Arenstein et al.

[11] Patent Number: 4,838,928

[45] Date of Patent: Jun. 13, 1989

[54] HERBICIDE

[75] Inventors: Zeev Arenstein, Petah Tiqua; Abraham Gotlieb, Kiryat Bialik, both of Israel

[73] Assignee: Agan Chemical Manufacturers Ltd., Ashdod, Israel

[21] Appl. No.: 120,764

[22] Filed: Nov. 16, 1987

Related U.S. Application Data

[63] Continuation of Ser. No. 841,823, Mar. 20, 1986, abandoned.

[30] Foreign Application Priority Data

Mar. 20, 1985 [IL] Israel ......................................... 74654

[51] Int. Cl.$^4$ ............................................. A01N 43/70
[52] U.S. Cl. ........................................ 71/93; 544/219; 71/79; 71/92; 71/105; 71/120
[58] Field of Search .............................. 71/93; 544/219

[56] References Cited

U.S. PATENT DOCUMENTS

| | | | |
|---|---|---|---|
| 2,909,420 | 10/1959 | Gysin et al. | 71/93 |
| 3,152,882 | 10/1964 | Luckenbaugh | 71/93 |
| 3,295,947 | 1/1967 | Kishikawa et al. | 71/93 |
| 3,676,441 | 7/1972 | Nikles | 71/93 |
| 3,873,298 | 3/1975 | Bieringer et al. | 71/93 |
| 4,640,705 | 2/1978 | Gabe et al. | 71/93 |

FOREIGN PATENT DOCUMENTS 2206048  6/1974  France ......................................... 71/93

OTHER PUBLICATIONS

Agrochemical Handbook, "Ametryn", pp. AO1-5–AO16, (Royal Society of Chemistry, 1983).

Duhr, "Weed Killing Effectiveness of Triazine Herbicides in Corn Crops, Etc.," Chem. Abstr. 93:90040k, (1980).

*Primary Examiner*—Glennon H. Hollrah
*Assistant Examiner*—A. A. Owens
*Attorney, Agent, or Firm*—Browdy & Neimark

[57] ABSTRACT

There is provided a postemergent herbicidal composition for use against broadleaved weeds. The composition comprises in combination terbutryne and ametryne in a weight ratio from 1 to 1.3 and up to 1 to 4. The compositions are of special value for use in plantations of cotton, corn and in a variety of orchards. They can be provided in the form of solutions, emulsifiable concentrates, wettable powders, flowable concentrates and the like.

11 Claims, No Drawings

HERBICIDE

This application is a continuation of application Ser. No. 841,823, filed Mar. 20, 1986 now abandoned.

FIELD OF THE INVENTION

The present invention concerns new compositions and a method of using these compositions in treating weeds in a variety of crops. More specifically the present invention concerns an economical method of controlling well-developed weeds such as broadleaved annuals with a synergistic combination of ametryne and terbutryne.

BACKGROUND OF THE INVENTION

Ametryne, 2-ethylamino-4-isopropylamino-6-methylthio-1,3,5-triazine, is a selective herbicide known since 1960. It has been used in pre- and post-emergence control of broad-leaved and grassy weeds in several types of crops. When used alone; however a high application rate is needed to affect well-developed weeds.

Terbutryne, 2-tert-butylamino-4-ethylamino-6-methylthio-1,3,5-triazine, is a selective herbicide primarily used in winter cereals, as described in Isrel Pat. No. 26950. It is primarily used as a pre-emergence herbicide with only weak post-emergence ability. In addition, when used alone even a rate as high as at 2 kg/ha, it only controls young, immature weeds.

There has been an ever increasing demand for an inexpensive post-emergence herbicide with good action against well developed broad-leaved weeds and especially against such weeds in the flowering stage.

SUMMARY OF THE INVENTION

We have surprisingly discovered that a mixture of terbutryne and ametryne is an effective postemergence herbicide. We have particularly discovered that a mixture of terbutryne and ametryne in a ratio of from 1:1.3 to 1:4 and preferably from 1:1.5 to 1:2 is a very potent post-emergence herbicide against broadleaved weeds and especially against broad-leaved weeds in cotton and well developed broad-leaved weeds in the flowering stage in orchards, cotton, corn etc.

Neither of these herbicides alone destroys well-developed broadleaves satisfactorily, while at the same time avoiding injury to the crops. It is only the combination of these two materials and especially in the specified ratios that provides satisfactory results with well-developed broad-leaved annual weeds, difficult to control using conventional herbicides.

Depending on the height and density of weeds, the terbutryne/ametryne mixture of the present invention is applied at a rate of 0.50 to 5.0 kg of active substance per hectare. Preferred dosages are between 1.0 and 3.5 kg of active substance per hectare with spray volumes of from 100 to 600 liters per hectare.

The mixture of this invention can be applied either separately or together it can be in the form of a solution, emulsifiable concentrate, wettable powder, flowable concentrate, or other formulated forms as are common in industry. The mixture of the present invention is preferably applied as a wettable powder.

The preferred wettable powders are dispersable in water and may be formed by mixing the essential herbicides with or without a carrier with a surface active agent. The carrier is preferably a solid, which may be finely divided. Examples of suitable solids are clays, sand, mica, solid fertilizers, chalk, attapulgite, diatomite, perlite, sepiolate, and synthetic solid carriers such as silicas, silicates, or lignosulfonates.

A preferred wettable powder comprises the two essential herbicides, kaoline and/or chalk as a carrier, and a surface active agent. Wettable powders of the present invention usually contain up to 80%, and preferably up to 65% in toto of the two active ingredients.

The term surface active agent is used in the broad sense to include materials variously called emulsifying agents, surfactants, dispersing agents, or wetting agents. Such agents are well known in the herbicide art.

The mixture of the present invention may be applied to plants, the soil, land, or aquatic areas. It is of particular interest for use as a post-emergence herbicide in cotton, in orchard crops, especially young orchards without any danger of phytotoxicity. The orchards include all types of cirtrus; deciduous such as peaches, plums, apricots, almonds, pecan and apples; subtropicals such as avocado, mango, cherimoya, litchi, and persimmon; as well as all varieties of grapes and olives. Very good results were obtained with cultivation of corn.

Some of the weeds controlled by the present invention are:
*Amaranthus graecizans*
*Amaranthus retroflexus*
Bidens sp.
Chrozophora sp.
Conyza sp.
*Ecbalium elaterium*
*Emex spinosa*
*Euphorbia geniculata*
Heliotropium sp.
Lamium sp.
Malva sp.
Moluccella sp.
*Portulaca oleracea*
Senecio sp.
Solanum eleaeagnifolium
*Solanum nigrum*
*Sonchus oleraceus*
Tribulus sp.
*Urtica pilulifera*

EXAMPLE 1

A wettable powder mixture of ametryne and terbutryne according to the present invention was prepared by mixing ametrex 80 WP (80% ametryne) with Terbutrex 50 WP (50% terbutryne)-each at a concentration of 0.5% formulated product. The resulting mixture was sprayed postemergence in a spray volume of 350 l/ha using a motorized knap-sack sprayer in a young citrus orchard in which were growing broadleaved weeds of 4-5 leaves such as Malva sp, Lamium sp, Senecio sp, *Sonchus oleraceus, Solanum nigrum, Urtica pilulifera, Emex spinosa* and grasses with four or more leaves. The results when applying the mixture of the present invention at 1.4 kg ametryne/ha and 0.9 kg terbutryne/ha were as follows:

| Weed | Percent Kill Days after Spray | |
|---|---|---|
| | 15 | 20 |
| Broadleaves | 90 | 100 |
| Grasses | — | 40 |

EXAMPLE 2

The mixture used in Example 1 was compared with a well known herbicidal mixture containing amitrole and simazine at a rate of 1 kg/ha and 1.5 kg/ha, respectively. The results were as follows:

| Weed | Percent Kill After 17 Days | |
|---|---|---|
| | Ametryne/Terbutryne | Amitrol/Simazine Control |
| Broadleaves | 100 | 75 |
| Grasses | 50 | 75 |

The mixture of the present invention killed the small, undeveloped grass weeds; but the very large grasses were only slightly damaged.

EXAMPLE 3

Following the same method and application rate as used in Example 1, the mixture of the present invention was used against various weeds in young avocado and citrus orchards, with the following results:

| Weed[f] | Percent Kill Days after Spray | | | | |
|---|---|---|---|---|---|
| | 11 | 18 | 25 | 30 | Control[a] |
| *Amaranthus retroflexus*[b] | 90 | 96 | 96 | 96 | 0 |
| *Conyza sp.*[c] | 80 | 90 | 95 | 95 | 0 |
| *Digitaria sanquinalis*[d] | 70 | 50 | 40 | 20 | 0 |
| *Portulaca oleracea*[e] | 90 | 100 | 100 | 100 | 0 |

[a]No spray
[b]Flowering plants,
[c]Flowering plants, 50–60 cm high
[d]Flowering plants
[e]A few flowers.
[f]All weeds are broadleaves except for *Digitaria sanguinalis* which is grass

EXAMPLE 4

The effect of the ametryne/terbutryne mixture in broadleaved weeds in various stages of flowering was studied in a young citrus orchard in two different compositions.
I. 1.4 kg/ha ametryne + 0.9 kg/ha terbutryne
II. 0.8 kg/ha ametryne + 0.5 kg/ha terbutryne
The results were as follows, using a spray volume of 350 l/ha.

| Weed[c] | Percent Kill Days After Spray | | | | | | | | |
|---|---|---|---|---|---|---|---|---|---|
| | 10 | | 15 | | 25 | | 40 | | |
| | I | II | I | II | I | II | I | II | Control |
| Amaranthus[a] | 80 | 65 | 95 | 75 | 96 | 77 | 98 | 57 | 0 |
| Conyza sp. | 80 | 80 | 90 | 90 | 100 | 100 | 100 | 100 | 0 |
| Portulaca | 60 | 35 | 100 | 100 | 100 | 100 | 100 | 100 | 0 |
| Malva sp. | 50 | — | 100 | — | 100 | — | 100 | — | 0 |
| *Digitaria sanguinalis* | 30 | 20 | 60 | 35 | 40 | 20 | 20 | 0 | 0 |
| *Solanum cleacagnifolium*[b] | 50 | 50 | 80 | 40 | 80 | 40 | 80 | 40 | 0 |

[a]*A. retroflexus* and *A. graecizans*
[b]Perennial
[c]All broadleaves except for *D. sanguinalis* which is a grass.

EXAMPLE 5

Following the method of Example 1, the effect of the ametryne/terbutryne mixture against annual broadleaves at various stages of development until flowering was compared in an avocado orchard with the effect of each component when applied alone. Weed species present were: Conyza sp, Amaranthus sp, Bidenspilosa, Polygonum sp. The results were as follows:

| Treatment | kg/ha | Percent Kill[a] Days after Spraying | | |
|---|---|---|---|---|
| | | 10 | 20 | 45 |
| Terbutryne | 0.9 | 37 | 37 | 25 |
| Ametryne | 1.4 | 50 | 63 | 50 |
| Terbutryne + Ametryne | 0.9 / 1.4 | 63 | 88 | 100 |
| Control | — | 0 | 0 | 0 |

[a]Effect was the same for each species. Terbutryne alone only partially scorched the weeds; but they were not killed. Ametryne alone seriously scorched the weeds and approximately 50% were killed. The mixture of ametryne and terbutryne, together gave the best results completely killing all the broadleaved annual weeds, including well-developed ones which are difficult to control using conventional herbicides.

EXAMPLE 6

Following the method of Example 5 and using the same application rates the ametryne/terbutryne mixture was compared with each component when applied alone in citrus orchards containing primarily flowering *Portulaca oleracea* The results were as follows:

| Treatment | Percent Kill Days after Spraying | | |
|---|---|---|---|
| | 10 | 20 | 45 |
| Terbutryne | 63 | 75 | 63 |
| Ametryne | 50 | 63 | 50 |
| Terbutryne + Ametryne | 75 | 100 | 100 |
| Control | 0 | 0 | 0 |

Terbutryne alone effectively scorched the Portulaca plants after 20 days; but later regrowth occurred from those parts of the plants not injured. Ametryne alone was less effective than terbutryne and did not cause a reduction in the weed population. However, the mixture of ametryne and terbutryne seriously scorched the weeds even after 10 days and caused complete kill after 20 days. After 40 days, regrowth only occurred from very few plants. In addition, while a large number of seeds germinated in the control plots, terbutryne or ametryne alone only prevented The emergence of weeds for 20 days. On the other hand, the mixture of ametryne and terbutryne prevented the emergence of weeds for 40 days.

EXAMPLE 7

The ametryne/terbutryne mixture of the present invention was compared with various other foliage applied herbicides and herbicidal mixtures with known activity against weeds. Five different compositions were used with a spray volume of 260 l/ha.

I. 2% Target (Target is a tradename for a formulation containing 480 g/l MSMA)

II. 1.5% Weedazol plus 0.75% Ametrex (Weedazol is a tradename for a mixture of 250 g/l amitrol and 220 g/l ammonium thiocyanate; Ametrex contains 80% ametryne)

III. 1.5% Weedazol

IV. 2% Target plus 0.75% Ametrex

V. 0.75% Terbutrex (50% terbutryne) plus 0.75% Ametrex

The results against weeds such as broadleaved annuals: Amaranthus sp, Conyza sp, Ecbalium elaterium; broadleaved perennials: Prosopis farcata Alhagi maurorum: l and grasses: Digitaria sanguinalis, Paspalum dialtatum, Setaria sp, in a peach orchard were as follows:

| Composition | kg/ha | Percent Kill Days after Spraying | |
|---|---|---|---|
| | | 21 | 37 |
| MSMA | 2.5 | 44 | 40 |
| Amitrol + | 1.0 | | |
| NH4SCN + | 0.9 | 70 | 66 |
| Ametryne | 1.6 | | |
| Amitrol + | 1.0 | 40 | 36 |
| NH4SCN | 0.9 | | |
| MSMA + | 2.5 | 60 | 64 |
| Ametryne | 1.6 | | |
| Terbutryne + | 1.0 | 80 | 82 |
| Ametryne | 1.6 | | |
| Control | | 0 | 0 |

The quantities given for Composition V are set forth in terms of the formulated product; in the table immediately above, the quantities given are provided on the basis of active ingredients.

The fifth composition, the mixture of the present invention, killed all the broadleaved weeds but did not affect the grasses and broadleaved perennials. The second composition strongly affected both broadleaved annual weeds and the grasses. The other compositions only had a moderate effect on the weeds. This experiment clearly shows the superior herbicidal activity of the terbutryne/ametryne mixture of the present invention when compared with known herbicides and herbicide mixtures.

EXAMPLE 8

The ametryne/terbutryne mixture of the present invention was compared in cotton with various other herbicides and herbicidal mixtures with known contact activity against weeds. Application was by directed spray between the rows of cotton plants when they were approximately 15 cm high and the weeds 10–15 cm high, using a spray volume of 400 l/ha.

7 different compositions were used as follows:

I. Terbutrex (50% terbutryne) 1.5 kg/ha+Ametrex (80% ametryne) 1.5 kg/ha.

II. Terbutrex 1.5 kg/ha+0.5% surfactant.

III. Ametrex 1.5 kg/ha+Diurex (80% diuron) 1.5 kg/ha.

IV. Ametrex 1.5 kg/ha+Simanex (50% simazine) 1.5 kg/ha.

V. Brominal (240 g/l bromoxynil) 2.0 l/ha+Target (480 g/l MSMA) 6 l/ha.

VI. Diurex 1.5 kg/ha+Target 6 l/ha+0.5% surfactant.

VII. Herbol (260 g/l MSMA+105 g/l sodium cacodylate+18 g/l cacodylic acid) 10 l/ha.

The results against broadleaved annuals such as Ecbalium elaterium, Moluccella sp., Heliotropium sp., Amaranthus sp, Chrozophora sp, were as follows:

| Composition | kg/ha of Active Ingredient | Percent kill 5 days after spraying |
|---|---|---|
| Terbutryne + | 0.75 | 62 |
| Ametryne | 1.2 | |
| Terbutryne + | 0.75 | 36 |
| Surfactant | 2.0 | |
| Ametryne + | 1.2 | 36 |
| Diuron | 1.2 | |
| Ametryne + | 1.2 | 44 |
| Simazine | 0.75 | |
| Bromoxynil + | 0.48 | 50 |
| MSMA | 2.9 | |
| Diuron + | 1.2 | 56 |
| MSMA + | 2.9 | |
| Surfactant | 2.0 | |
| MSMA + | 2.6 | 38 a* |
| Sodium cacodylate + | 1.1 | |
| Cacodylic acid | 0.2 | |
| Control | | 0 |

*a = damage to cotton

The quantities given for Composition I are set forth in terms of the formulated product; the quantities given in the table above are provided on the basis of active ingredients.

The first composition, the mixture of the present invention, was the most effective treatment and was not phytotoxic to the cotton.

EXAMPLE 9

Following the method of Example 8, the ametryne/terbutryne mixture was compared with an ametryne/MSMA mixture which is known to be an effective contact herbicidal composition. The height of the cotton plants at application was 25–30 cm and that of the weeds 5–15 cm (up to 9 leaves), with using a spray volume of 140 l/ha.

The results against the difficult to control broadleaved weed, Euphorbia geniculata were as follows:

| Treatment | kg/ha | Percent kill Days after spraying | |
|---|---|---|---|
| | | 3 | 7 |
| Ametryne + | 0.8 | 43 | 80 |
| Terbutryne | 0.5 | | |
| Ametryne + | 1.2 | 67 | 90 |
| Terbutryne | 0.8 | | |
| Ametryne + | 1.2 | 26 | 87 |
| MSMA[a] | 1.0 | | |
| Control | — | 0 | 0 |

[a]Target (480 g/l MSMA).

The higher rates of the ametryne/terbutryne mixture provided more rapid and effective weed control when compared with the ametryne/MSMA mixture which is in current use as a directed contact herbicidal treatment. The ametryne/terbutryne mixture was not damaging to the cotton plants.

We claim:

1. A postemergent herbicidal composition for use against broadleaved weeds comprising in combination terbutryne and ametryne in a weight ratio of from 1:1.3 to 1:3.

2. A composition according to claim 1, wherein the weight ratio is from 1:1.5 to 1:2.

3. A composition according to claim 1 in the form of a solution, or wettable power and further comprising an inert agricultural carrier, said combination of terbutryne and ametryne being present in an herbicidally effective amount.

4. A method of controlling broadleaved weeds which compises applying to the locus of same an herbicidally effective amount of composition as claimed in claim 1.

5. A method according to claim 4, wherein the application is to post-emergent weeds.

6. A method according to claim 5, wherein the composition is applied to weeds in plantations of cotton, corn, in orchards olives or grapes.

7. A method according to claim 5, wherein the compositions are applied at a rate of 1.0 kg to 3.5 kg active ingredient per hectare.

8. A method as claimed in claim 5, wherein the weight ratio of terbutryne to ametryne in the composition is from 1:1.5 and up to 1:2.

9. A composition according to claim 2 in the form of a solution, or wettable powder and further comprising an inert agricultural carrier, said combination of terbutryne and ametryne being present in an herbicidally effective amount.

10. A method according to claim 5 wherein at least some of said post-emergent weeds are at the flowering stage.

11. A method of killing broad leafed weeds at the flowering stage among crops of cotton, corn, citrus fruits, olives, grapes, almonds, avocado, mango, cherimoya, or litchi, comprising applying to post-emergent broad leafed weeds at the flowering stage an herbicidally effective amount in the range of about 1.0 kg to 3.5 kg per hectare of terbutryne and ametryne in a weight ratio of 1:1.3 to 1:3.

* * * * *